US00PP33928P2

(12) United States Plant Patent
O'Connell

(10) Patent No.: US PP33,928 P2
(45) Date of Patent: Feb. 1, 2022

(54) ***CRASSULA* PLANT NAMED 'DAYDREAM'**

(50) Latin Name: *Crassula capitella*
Varietal Denomination: Daydream

(71) Applicant: Altman Specialty Plants, Inc, Vista, CA (US)

(72) Inventor: Renee O'Connell, Escondido, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 17/357,595

(22) Filed: Jun. 24, 2021

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 5/00; A01H 5/12
See application file for complete search history.

*Primary Examiner* — Kent L Bell
(74) *Attorney, Agent, or Firm* — Cassandra Bright

(57) ABSTRACT

A new and distinct variety of *Crassula* plant named 'Daydream' is disclosed, characterized by an unusual, stable, tricolor variegation, comprised of leaves with cream yellow margins, tipped with raspberry and often blushing rose in cooler weather. The central areas of the leaves are apple green, and exhibit occasional splashes of rose or cream yellow. In addition, the new cultivar 'Daydream' offsets heavily, enhancing production in the commercial nursery. The new variety is a *Crassula*, part of the Crasulaceae family that includes *Crassula, Pachyphytum, Graptopetalum, Sedum* and others. *Crassula* is a popular genus, typically produced as container plants or as landscape plants.

2 Drawing Sheets

Latin name of the genus and species: *Crassula capitella.*
Variety denomination: 'DAYDREAM'.

BACKGROUND OF THE INVENTION

The new cultivar, *Crassula* 'Daydream', was found in an existing population of propagation stock plants of an unnamed variety of *Crassula capitella* in a commercial greenhouse in Vista, Calif. by the inventor. *Crassula* 'Daydream' is a naturally occurring branch mutation of the unnamed *Crassula capitella*. The new cultivar, *Crassula* 'Daydream' was discovered by the inventor in October of 2015.

Asexual reproduction of the new cultivar 'Daydream' was first performed in Vista, Calif., at a commercial greenhouse, by vegetative cuttings in February of 2016. 'Daydream' has since produced multiple generations and has shown that the unique features of this cultivar are stable and reproduced true to type.

SUMMARY OF THE INVENTION

The cultivar 'DAYDREAM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DAYDREAM' These characteristics in combination distinguish 'DAYDREAM' as a new and distinct *Crassula* cultivar:

1. The new cultivar *Crassula* 'Daydream' exhibits tricolor coloration, not exhibited by many other *Crassula.*
2. *Crassula* 'Daydream' displays leaves with cream yellow margins, tipped with raspberry and often blushing rose in cooler weather. The central areas of the leaves are apple green, and exhibit occasional splashes of rose or cream yellow.
3. *Crassula* 'Daydream' offsets heavily, and is fast growing, enhancing production in the commercial nursery environment.

Plants of the new cultivar 'DAYDREAM' are similar to plants of the parent in most horticultural characteristics, however, plants of the new cultivar 'DAYDREAM' differ in the following;

1. *Crassula* 'Daydream' exhibits variegated coloration, which is not seen in the parent.
2. *Crassula* 'Daydream' exhibits an attractive rose blush, particularly to the leaf tips, but often on the overall leaf during the cooler months, whereas the parent displays a more red blush during the cooler months.
3. As *Crassula* 'Daydream' exhibits less chlorophyl in its coloration, it is not quite as fast growing as the parent.

COMMERCIAL COMPARISON

Plants of the new cultivar 'DAYDREAM' are comparable to the unpatented, commercial variety *Crassula ovata* 'Tricolor'. The two *Crassula* varieties are similar in most horticultural characteristics; however, the new variety 'DAYDREAM' differs in the following:

1. *Crassula* 'Daydream' exhibits apple green leaves with pale yellow margins, tipped with raspberry and often blushing rose in cooler weather, whereas *Crassula ovata* 'Tricolor' displays frosted green leaves with cream colored marginal areas, and variable longitudinal "striping" of dark green, and cream.

2. *Crassula* 'Daydream' is a heavily offsetting compact plant, whereas *Crassula ovata* 'Tricolor' displays a branching, arborescent morphology, attaining a mature height of 3'+.
3. Whereas the leaves of *Crassula ovata* 'Tricolor' are thickened and fleshy, the leaves of *Crassula* 'Daydream' are much thinner.
4. *Crassula ovata* 'Tricolor' produces a thickened, bark-like trunk with maturity, whereas *Crassula* 'Daydream' does not.
5. *Crassula* 'Daydream' grows more quickly than does *Crassula ovata* 'Tricolor'.

Plants of the new cultivar 'DAYDREAM' can also be comparable to an unpatented, unnamed variety of *Crassula tetragona* found in the horticultural market. The two *Crassula* varieties are similar in most horticultural characteristics; however, the new variety 'DAYDREAM' differs in the following:

1. *Crassula* 'Daydream' produces a compact clustering plant, whereas this comparator is a more arborescent plant, forming clusters of thick stems.
2. *Crassula* 'Daydream' exhibits somewhat rounded apple green leaves, with pale yellow margins and often blushing raspberry at the leaf apices. During cooler weather, the leaves can become tinged with raspberry. In contrast, this comparator has laterally placed, stiff, slender, cylindrical green leaves on arborescent stalks.
3. *Crassula* 'Daydream' prefers bright, filtered light, whereas this comparator is more suited to full sun.
4. *Crassula* 'Daydream' is fast growing, whereas this comparator grows more slowly.

BRIEF DESCRIPTION OF THE PHOTOGRAPHS

The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new cultivar *Crassula* 'Daydream'.

DETAILED BOTANICAL DESCRIPTION

Figure 1:
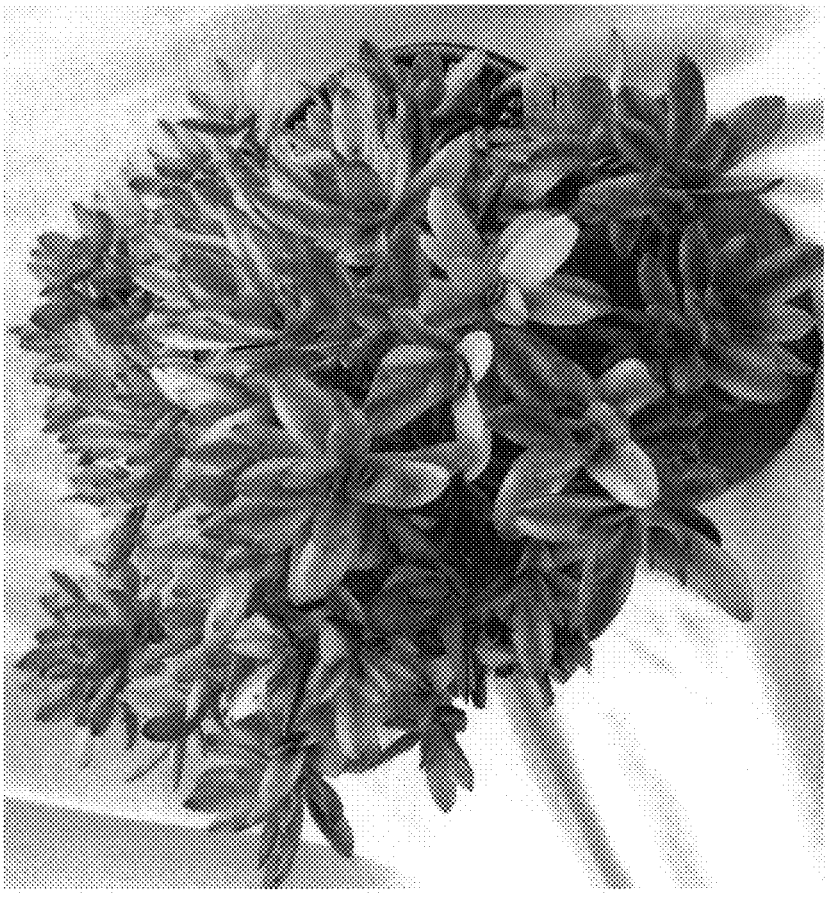
FIG. 1 illustrates in full color a plant of *Crassula* 'Daydream', at about 9 months, grown at a nursery (approximately 2500 foot candles) in Vista, Calif.
Figure 2:
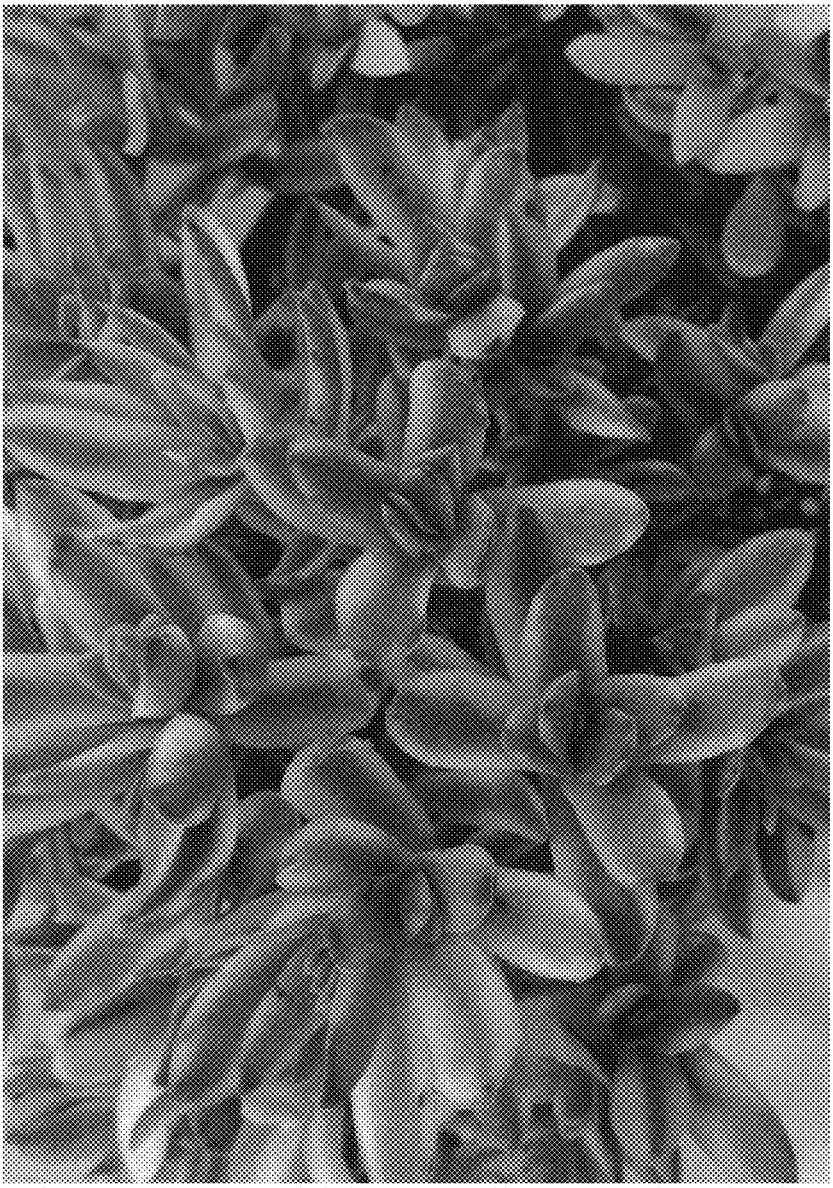
FIG. 2 illustrates in full color a closer view of the foliage of the plant of FIG. 1.

In the following description, color references are made to The Royal Horticultural Society Colour Chart, 2007 edition, except where general terms of ordinary dictionary significance are used. The following observations and measurements describe 'Daydream' plants grown in a commercial nursery in Vista, Calif. Temperatures ranged from about 2° C. to 39° C. No artificial light, photoperiodic treatments or chemical treatments were given to the plants. Natural light conditions were approximately 2500 to 3000 fc of light. Measurements and numerical values represent averages of typical plant types.

Botanical classification: *Crassula capitella* 'DAYDREAM'.

Propagation:

Type of propagation typically used: Terminal vegetative divisions.

Time to initiate roots: About 16 days at approximately 25° C.

Root description: Fibrous.

Plant:

Age of plant described: Approximately 9 months.

Container size of the plant described: 1 gallon pot.

Growth habit: Multi-branched shrublet.

Height: Approximately 12 cm.

Plant spread: Approximately 28 cm.

Growth rate: Moderately fast.

Branching characteristics: Abundant sub-opposite lateral branches. About 4 breaks from a pinch on average.

- *Length*.—Main branches about 5 cm to 8 cm, lateral branches about 5 cm to 10 cm.
- *Width*.—5 mm.
- *Color*.—Lowermost colored near Greyed-Orange 174D. Uppermost Yellow-Green 144D.
- *Texture*.—Glabrous.
- *Strength*.—Moderately strong.
- *Internode*.—About 1 cm.

Foliage:

Leaf:

- *Arrangement*.—Opposite decussate.
- *Average length*.—Approximately 2.5 to 3.0 cm.
- *Widest width*.—Approximately 8 to 11 mm.
- *Shape of blade*.—Oblanceolate.
- *Apex*.—Acute.
- *Base*.—Truncate.
- *Margin*.—Entire to very minutely deritate.
- *Texture of top surface*.—Glabrous.
- *Texture of bottom surface*.—Glabrous.
- *Quantity of leaves per plant*.—Average 16 to 24 per branch.
- *Color*.—Young foliage upper side: Center near Green 138B, thick margins near Yellow-White 158D, overall, slightly flushed Red-Purple 61D. Young foliage, under side: Center near Green 138B, thick margins near Yellow-White 158D, overall strongly flushed. Red-Purple 61B. Mature foliage upper side: Center near Green 138B, thick margins near Yellow-White 158D. Marginal flush near Red-Purple 61B. Mature foliage upper side: Center near Green 138B, thick margins near Yellow-White 158D. Marginal flush near Red-Purple 61B.
- *Venation*.—Indistinguishable from leaf blade.

Flower: Flowering not observed to date.

Reproductive organs: Unknown, flower has not yet been observed.

Other characteristics:

- *Fruits and seeds*.—Unknown; has not flowered to date.
- *Temperature tolerance*.—Tolerates temperatures from approximately 2° C. to 39° C.
- *Disease/pest resistance*.—No increased nor decreased resistance to normal diseases and pests of *Crassula* has been observed.
- *Drought tolerance*.—Tolerates at least 3 weeks of high temperatures without supplemental water, showing no serious damage to plant.

What is claimed is:

1. A new and distinct cultivar of *Crassula* plant named 'DAYDREAM' as herein illustrated and described.

* * * * *